United States Patent [19]
Kottke et al.

[11] Patent Number: 5,529,902
[45] Date of Patent: Jun. 25, 1996

[54] DIRECT FLUORESCENCE-CONJUGATED IMMUNOASSAY FOR PLATELET ACTIVATION

[75] Inventors: Bruce A. Kottke, Lakeland, Fla.; Deyong Wen, Rochester, Minn.

[73] Assignee: Mayo Foundation for Medical Education and Research, Rochester, Minn.

[21] Appl. No.: 377,679

[22] Filed: Jan. 27, 1995

Related U.S. Application Data

[63] Continuation of Ser. No. 142,766, Oct. 26, 1993, abandoned.
[51] Int. Cl.$^6$ ............... G01N 33/533; G01N 33/536; G01N 33/577
[52] U.S. Cl. ............... 435/7.21; 435/28; 436/172; 436/536; 436/548; 530/388.1; 530/388.22
[58] Field of Search ............... 435/7.21, 28; 436/172, 436/536, 548; 530/388.1, 388.22

[56] References Cited

U.S. PATENT DOCUMENTS 4,783,330  11/1988  Furie et al. ............... 436/519

OTHER PUBLICATIONS

Metzelaar, M. J., et al. Biochemical and immunohistochemical characteristics of CD62 and CD63 monoclonal antibodies. Virchows Archiv. B Cell. Pathol. 61:269–277, 1991.

Berman, C. L., et al. A platelet alpha-granule membrane protein that is associated with the plasma membrane after activation. J. Clin. Invest. 78:130–137, 1986.

Harlowe, E. et al. Antibodies: A Laboratory Manual. Cold Spring Harbor, NY: Cold Spring Harbor Laboratory, pp. 354 & 359–419, 1988.

Metzelaar, M. J., et al. Comparison of platelet membrane markers for the detection of platelet activation in vitro and during platelet storage and cardiopulmonary bypass surgery. J. of Clin. Lab. Med. 121 (4) 579–587, 1993.

Accurate Antibodies Catalog 1993. p. 54.

C. S. Abrams et al., "Direct Detection of Activated Platelets and Platelet–Derived Microparticles in Humans", *Blood*, 75, 128–138 (1990).

R. Bonfanti et al., "PADGEM (GMP140) is a Component of Weibel–Palade Bodies of Human Endothelial Cells", *Blood*, 73, 1109–1112 (Apr. 1989).

J. G. Diodati et al., "Platelet Hyperaggregability Across the Coronary Bed in Response to Rapid Atrial Pacing in Patients with Stable Coronary Artery Disease", *Circulation*, 86, 1186–1193 (Oct. 1992).

D. J. Fitzgerald et al., "Marked platelet activation in vivo after intravenous streptokinase in patients with acute myocardial infarction", *Circulation*, 77, 142–150 (Jan. 1988).

J.–G. Geng et al., "Purified GMP–140 is a Receptor for Neutrophils", *Blood*, 74, 65a, Abstract No. 234 (1989).

F. George et al., "Rapid Isolation of Human Endothelial Cells from Whole Blood Using S–Endol Monoclonal Antibody Coupled to Immuno–Magnetic Beads: Demonstration of Endothelial Injury after Angioplasty", *Thrombosis and Haemostasis*, 67, 147–153 (1992).

J. N. George et al., "Platelet Surface Glycoproteins", *J. Clin. Invest.*, 78, 340–348 (Aug. 1986).

A. H. Gershlick, "Are There Markers of the Blood–Vessel Wall Interaction and of Thrombus Formation that Can Be Used Clinically?", *Supplement I Circulation*, 81, I–28–I–34 (Jan. 1990).

(List continued on next page.)

*Primary Examiner*—Toni R. Scheiner
*Assistant Examiner*—Nancy J. Parsons
*Attorney, Agent, or Firm*—Schwegman, Lundberg & Woessner

[57] ABSTRACT

A method is provided to measure the extent of platelet activation by fluorometrically determining the extent of expression of P-selectin in a platelet sample in vitro, using a maximally activated platelet sample as a reference standard.

10 Claims, 7 Drawing Sheets

OTHER PUBLICATIONS

S. A. Hamburger et al., "GMP-140 Mediates Adhesion of Stimulated Platelets to Neutrophils", *Blood*, 75, 550–554 (Feb. 1990).

C. W. Hamm et al., "Biochemical Evidence of Platelet Activation in Patients with Persistent Unstable Angina", *JACC*, 10, 998–1004 (Nov. 1987).

G. I. Johnston et al., "Cloning of GMP-140, a Granule Membrane Protein of Platelets and Endothelium: Sequence Similarity to Proteins Involved in Cell Adhesion and Inflammation", *Cell*, 56, 1033–1044 (Mar. 1989).

E. Larson et al., "PADGEM Protein: A Receptor That Mediates the Interaction of Activated Platelets with Neutrophils and Monocytes", *Cell*, 59, 305–312 (Oct. 1989).

J. Lavee et al., "Platelet Protection by Aprotinin in Cardiopulmonary Bypass: Electron Microscopic Study", *Ann. Thorac. Surg.*, 53, 477–481 (1992).

T. L. Lindahl et al., "Studies of Fibrinogen Binding to Platelets by Flow Cytometry: An Improved Method for Studies of Platelet Activation", *Thrombosis and Haemostasis*, 68, 221–225 (1992).

E. Minar et al., "Platelet Deposition at Angioplasty Sites and Its Relation to Restenosis in Human Iliac and Femoropopliteal Arteries", *Radiology*, 170, 7–772 (Mar. 1989).

H. Ogawa et al., "Plasma Platelet-Derived Growth Factor Levels in Coronary Circulation in Unstable Angina Pectoris", *Am. J. Cardiol.* 69, 453–456 (Feb. 15, 1992).

T. M. Palabrica et al., "Thrombus imaging in a primate model with antibodies specific for an external membrane protein of activated platelets", *Proc. Natl. Acad. Sci. USA*, 86, 1036–1040 (Feb. 1989).

S. Parmentier et al., "New families of adhesion molecules play a vital role in platelet functions", *Immunology Today*, 11, 225–227 (1990).

E. I. B. Peerschke, "Platelet Membrane Glycoproteins", *Clinical Pathology*, 98, 455–463 (Oct. 1992).

G. Rasmanis et al., "Evidence of increased platelet activation after thrombolysis in patients with acute myocardial infarction", *Br. Heart J.*, 68, 374–376 (1992).

B. Savage et al., "Modulation of Platelet Function through Adhesion Receptors", *J. Biol. Chem.*, 267, 11300–11306 (Jun. 1992).

R. M. Scarborough et al., "Characterization of the Integrin Specificities of Disintegrins Isolated from American Pit Viper Venoms", *J. Biol. Chem.*, 268, 1058–1065 (Jan. 1993).

R. E. Scharf et al., "Activation of Platelets in Blood Perfusing Angioplasty-Damaged Coronary Arteries", *Arteriosclerosis and Thrombosis*, 12, 1475–1487 (Dec. 1992).

R. S. Schwartz et al., "Restenosis and the Proportional Neointimal Response to Coronary Artery Injury: Results in a Porcine Model", *JACC*, 19, 267–274 (Feb. 1992).

S. J. Shattil et al., "Detection of Activated Platelets in Whole Blood Using Activation Dependent Monoclonal Antibodies and Flow Cytometry", *Blood*, 70, 307–315 (Jul. 1987).

P. E. Stenberg et al., "A Platelet Alpha-Granule Membrane Protein (GMP-140) is Expressed on the Plasma Membrane after Activation", *J. Cell Biology*, 101, 880–886 (Sep. 1985).

Y. Tomiyama et al., "The Arg-Gly-Asp (RGD) Recognition Site of Platelet Glycoprotein IIb-IIIa on Nonactivated Platelets Is Accessible to High-Affinity Macromolecules", *Blood*, 79, 2303–2312 (May 1992).

D. J. Tschoepe et al., "Platelet Activation is Predictive for an Increased PTCA Risk", *Thrombosis Council Abstracts*, 1159a.

D. Tschoepe et al., "Platelet Membrane Activation Markers are Predictive for Increased Risk of Acute Ischemic Events After PTCA", *Circulation*, 88, 37–42 (Jul. 1993).

A. C. van Hof et al., "Assessment of Whole-Blood Spontaneous Platelet Aggregation during Pregnancy Using an Impedance Particle Counter", *Haemostasis*, 22, 160–164 (1992).

T. E. Warkentin et al., "Measurement of fibrinogen binding to platelets in whole blood by flow cytometry: a micromethod for the detection of platelet activation", *British Journal of Haematology*, 76, 387–394 (1990).

I. Weinberger et al., "Circulating Aggregated Platelets, Number of Platelets per Aggregate, and Platelet Size during Acute Myocardial Infarction", *Am. J. Cardiol.*, 70, 981–983 (Oct. 1992).

J. W. Weisel et al., "Examination of the Platelet Membrane Glycoprotein IIb-IIIa Complex and Its Interaction with Fibrinogen and other Ligands by Electron Microscopy", *J. Biol. Chem.*, 267, 16637–16643 (Aug. 1992).

R. N. Willette et al., "Antithrombotic Effects of a Platelet Fibrinogen Receptor Antagonist in a Canine Model of Carotid Artery Thrombosis", *Stroke*, 23, 703–711 (May 1992).

DIRECT FLUORESCENCE-CONJUGATED IMMUNOASSAY FOR PLATELET ACTIVATION

This is a continuation of application Ser. No. 08/142,766, filed Oct. 26, 1993, now abandoned.

BACKGROUND OF THE INVENTION

P-selectin, also known as granule membrane protein-140 (GMP-140), or PADGEM protein, is an integral membrane glycoprotein found in secretory granules of both platelets and endothelial cells. See E. I. B. Peerschke, *Am. J. Clin. Pathol.*, 98, 455 (1992). After activation of these cells by agonists such as thrombin, it is rapidly redistributed to the cell surface during degranulation. P-selectin belongs to the selectin family of vascular cell surface receptors that share sequence similarity and overall domain organization. See G. I. Johnston et al., *Cell*, 56, 1033 (1989). The other known selectins are ELAM-1, a cytokine-inducible endothelial cell receptor for neutrophils, and a leukocyte surface structure which plays a role in directing the homing of lymphocytes to high endothelial venules of peripheral lymph nodes. It has recently been shown by J.-G. Geng et al., *Blood*, 74, 65a (1989), that human neutrophils bind in a $Ca^{2+}$-dependent manner to purified P-selectin immobilized on plastic. Furthermore, adhesion of neutrophils to endothelium stimulated with rapid activators such as histamine is mediated at least in part by P-selectin. P-selectin is also involved in binding of activated platelets to monocytes and neutrophils. See, S. A. Hamburger et al., *Blood*, 75, 550 (1990) and E. Larsen, *Cell*, 59, 305 (1989).

Because platelet activation accompanies a number of vascular disorders such as unstable angina, peripheral vascular disease, stroke, and procedures such as angioplasty and coronary thrombolysis, considerable effort has been exerted during the last two decades to develop more sensitive and specific methods to detect activated, circulating platelets. See, for example, C. W. Hamm et al., *J. Am. Coll. Cardiol.*, 10, 998 (1987); D. J. Fitzgerald et al., *Circulation*, 77, 142 (1988) and A. H. Gershlick, *Circulation*, 81, 128 (1991). The most reliable markers of in vivo platelet activation have been substances released from platelets after activation, which can be measured in the plasma or urine: platelet factor 4 (PF4), β-thromboglobulin (β-TG), and metabolites of thromboxane $A_2$. These markers have not achieved widespread clinical acceptance, however, because of technical limitations pertaining to sample collection, processing, and analysis.

Several changes in surface membrane glycoprotein expression can be detected during platelet activation with specific murine monoclonal antibodies. For example, as reported by S. J. Shattil, in *Blood*, 70, 307 (1987), and C. S. Abrams et al., *Blood*, 75, 128 (1990), changes in the conversion of the GPIIb-IIIa complex to a functional fibrinogen receptor can be detected. J. N. George et al., *J. Clin. Invest.*, 78, 340 (1986) reported that platelet activation with accompanying alpha granule release can be ascertained by examining P-selectin expression. Thus, assays have been designed that combine the use of activation-specific monoclonal antibodies with flow cytometry. See, for example, R. E. Scharf et al., *Arteriosclerosis and Thrombosis*, 12, 1475 (1992). These assays can be performed on whole blood and can facilitate the detection of platelet subpopulations that are heterogeneous with respect to their activation status. However, flow-cytometry requires expensive instrumentation, complex data processing and is not practical either to process large numbers of samples economically or to derive results within the timeframe required to affect clinical outcomes in acute situations such as those mentioned above.

Therefore, a need exists for a sensitive, simple and rapid in vitro assay to detect the extent of platelet activation.

SUMMARY OF THE INVENTION

The present invention provides a method to determine the extent of mammalian platelet activation. The platelets preferably are isolated in vitro from a sample of physiological material, such as human blood, saliva, urine, CSF and the like, and divided into two portions, preferably containing equivalent numbers of platelets. One sample is then maximally activated, employing a suitable agonist such as ADP, while the other sample is not treated with exogenous activation agonists. Anti-P-selectin antibody is then added to each sample in an amount effective to bind to the activated platelets in each sample. The antibody-activated platelet complexes in each sample are determined fluorometrically, by means of a fluorescent label that is attached to the anti-P-selectin antibody, or by addition to the complexes of a fluorescent label which binds to a binding site on the bound antibody. A ratio of the fluorescence of the complexed activated platelets in the sample not exogenously activated to the fluorescence of the maximally activated platelets provides a measure of the extent of platelet activation in the mammalian donor of the platelets.

Thus, the present invention provides a fluorescence-conjugated immunobinding assay (FCIBA), for measuring platelet activation comprising:

(a) isolating in vitro a first sample of platelets and a second sample of platelets from a mammal, wherein said sample each contains a preselected number of platelets;

(b) adding an amount of an activation agonist such as adenosine 5'-diphosphate (ADP) to said first sample in a liquid medium for a period of time effective to activate and aggregate all of the activatable platelets in said first sample; while maintaining the second sample in a liquid medium for an equivalent period of time;

(c) adding an amount of
  (i) an anti-P-selectin antibody comprising a fluorescent label; or
  (ii) an anti-P-selectin antibody comprising a binding site for a detectable fluorescent label followed by a detectable fluorescent label; so as to form binary labelled complexes with the activated platelets in each sample; and (d) determining the fluorescence of the binary labelled complexes in each sample, wherein a ratio of the fluorescences provides a measure of the extent of platelet activation in said second sample.

The steps of one embodiment of the present assay are outlined in FIG. 1. As noted above, preferably the platelets are isolated from a tissue or a physiological fluid such as human blood, e.g., the first and second samples comprise platelet-rich plasma (PRP). The PRP samples can be diluted with a compatible liquid medium such as platelet-poor plasma (PPP), PBS, isotonic saline and the like, so that the samples which are processed contain essentially identical numbers of platelets. The liquid medium can also include an anti-clotting agent.

To develop the assay, platelet samples were activated with various doses of ADP and fixed platelets were incubated with a fluorescence-conjugated anti-P-selectin antibody in wells of microtiter plates. The fluorescence intensity was read on a fluorescence concentration analyzer. Once the platelet samples were fixed, the data collection/analysis procedures can be completed in less than two hours. The intra-assay coefficient of variation (CV) was 6.97%, the time-based inter-assay CV was 8.11% and the sample-based inter-assay CV was 6.17%. The present assay demonstrates an excellent correlation (r=0.936) with flow cytometry in the measurement of expressed P-selectin in platelets of 20 normal donors.

Unexpectedly, the translocation of P-selectin in platelets in response to increasing doses of ADP occurred in a dose-dependent manner and correlated positively with ADP-induced platelet aggregation in the aggregometer on the basis of both stimulating doses of ADP (r=0.99) and on the basis of time intervals (r=0.92).

The amount of fibrinogen detected on the surface of the platelets was also increased in response to ADP, whereas the intensity of bound antibodies to the GPIIb-IIIa complex underwent little alteration. In activated platelets, the intensity of fibrinogen antibody binding was correlated with the intensity of P-selectin antibody binding (r=0.85).

These results demonstrate that the present invention provides a rapid and uncomplicated assay for platelet activation via determination of surface antigens present or activated human platelets, and that P-selectin is a more sensitive and specific marker than the GPIIb-IIIa complex or than fibrinogen for platelet activation.

Thus, the present assay can be used to evaluate, monitor and stage platelet activation-related events associated with acute coronary syndromes, and in retenosis following percutaneous transfemoral coronary angioplasty (PTCA). With respect to the role of circulating activated platelets in these states, see, for example, I. Weinberger et al., *Am. J. Card.*, 70, 981 (1992); E. Minar et al., *Card.*, 170, 767 (1989); R. S. Schwartz et al., *J. Am. Col. Card.*, 19, 267 (1992) and D. Tshoepe et al., *Circ.*, 88, 37 (1993).

DETAILED DESCRIPTION OF THE INVENTION

Figure 1:
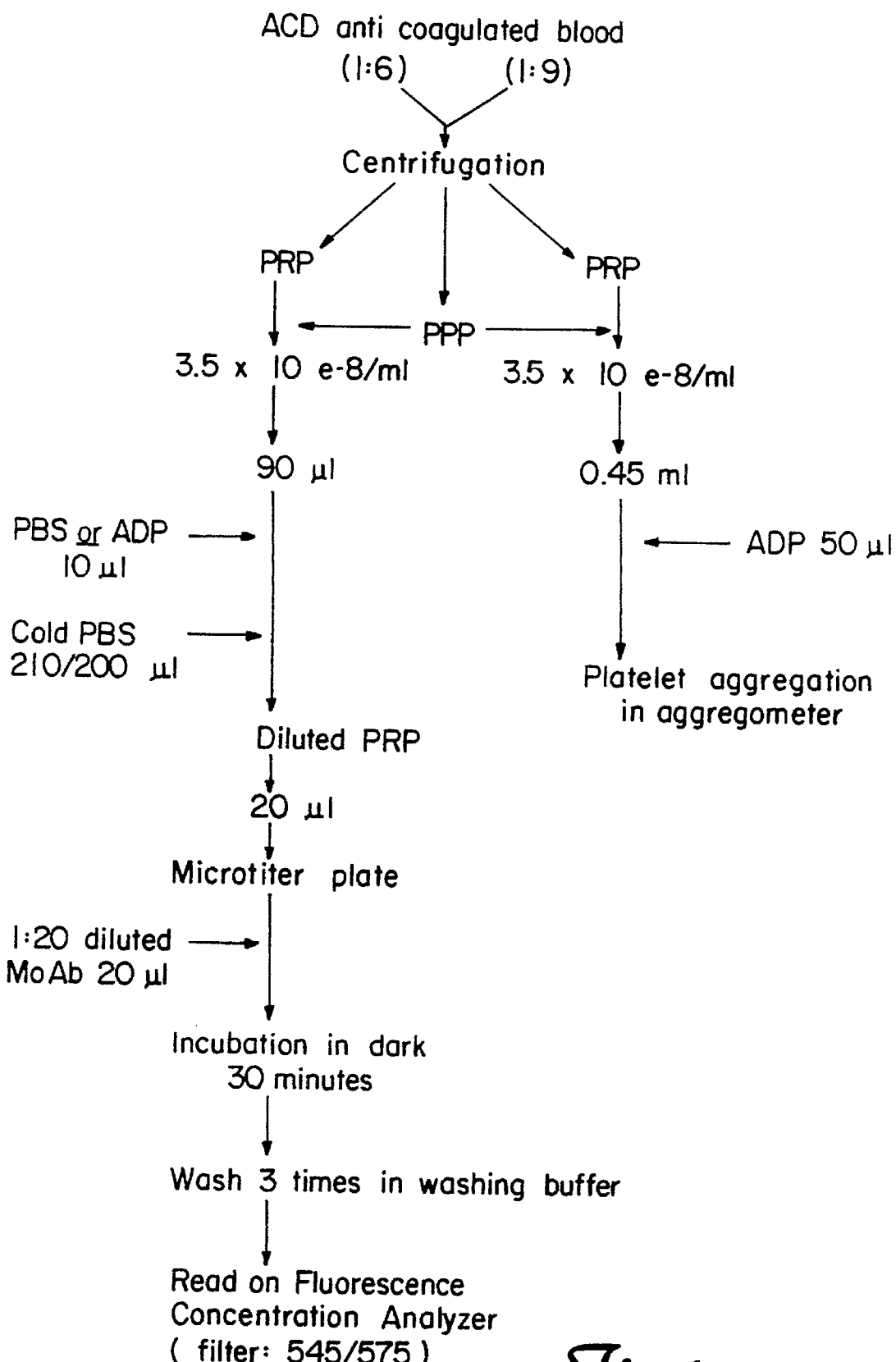
FIG. 1 is a schematic depiction of one embodiment of the present assay.

Monoclonal antibodies and polyclonal antibody preparations comprising fluorescent labels or binding sites for ligands comprising fluorescent labels are commercially available, available to the art or preparable by art-recognized procedures. Representative murine anti-P-selectin antibodies are listed in Table I, below.

TABLE I

| Anti-P-Selectin Antibody | Label | Reference |
| --- | --- | --- |
| S12 | Fluorescein or phyoerythrin | R. E. Scharf et al., Arteriosclerosis and Thrombosis, 12, 1475 (1992); R. P. McEver et al., J. Biol. Chem., 259, 9799 (1984). |
| | — | P. E. Stenberg et al., J. Cell. Biol., 101, 880 (1985). |
| KC4 | — | S. C. Hsu-Lin et al., J. Biol. Chem., 259, 9121 (1984); R. Bonfanti et al., Blood, 73, 1109 (1989). |
| AC1.2; 1–18, 2–15, 2–17 | — | E. Larsen et al., Cell, 59, 305 (1989). |
| CD62 | Phycoerythrin or no label | Becton-Dickinson |
| G1 | — | S. A. Hamburger et al., Blood, 75, 550 (1990). |

Unlabelled antibodies can be conjugated to fluorescent labels such as fluorescein isocyanate (FITC) by standard techniques. See, for example, S. J. Shattil et al., Blood, 70, 307 (1987) and J. W. Goding et al., Monoclonal Antibodies: Principles and Practice—Production and Application of Monoclonal Antibodies in Cell Biology, Biochemistry and Immunology, Academic Press, London (1986) at pages 255–280. Alternatively, the antibodies can be prepared as biotinylated conjugates and reacted with phycoerythrin-streptavidin as taught by Goding, ibid., McEver et al., ibid., and S. J. Shattil et al., J. Biol. Chem., 260, 11107 (1985). Polyclonal anti-P-selectin antibody preparations can be prepared and detected as taught by P. E. Stenberg, J. Cell Biol., 101, 880 (1985).

Although ADP is a preferred platelet activation-aggregation agonists, other useful agents for platelet activation include thrombin, serotonin, collagen and throboxane, as well as bioactive subunit polypeptides thereof.

The invention will be further described by reference to the following detailed examples, wherein adenosine diphosphate (ADP, Catalog No. 885-3), paraformaldehyde (Catalog No. 62H0174) and other chemicals were obtained from Sigma (Sigma Chemical Co., St. Louis, Mo.). Phycoerythrin (PE)-conjugated (Catalog No. 348107) and pure (Catalog. No. 348100) murine monoclonal anti-human platelet P-selectin antibodies (CD62) and PE-conjugated isotype specific mouse IgG1 (Catalog No. 340013) were purchased from Becton-Dickinson (Mountain View, Calif.). FITC-conjugated murine monoclonal anti-human platelet GPIIb-IIIa antibody (CD41a) (Catalog No. 0649) was obtained from AMAC (Westbrook, Me.). FITC-conjugated sheep anti-human fibrinogen antibody (Catalog No. K90056F) was obtained from BIO-DESIGNE (Kennebunkport, Me.). Antibodies were diluted using 1% fetal calf serum phosphate-buffered saline (PBS) solution.

Ten aspirin-free normal donors (age: 24–41, male: 5, female: 5) were recruited through the healthy donor center at Mayo Clinic. Blood was drawn in a 21 gauge butterfly needle and a plastic syringe and collected using 15 ml polypropylene centrifuge tubes (Corning Inc.) containing 1:6 (for platelet activation) and 1:9 (for platelet aggregation) volumes of acid citrate dextrose (ACD). Blood samples were centrifuged at 250 xg for 10 minutes at 15° C. in a Mistral 3000-i centrifuge with rate of 5 for brake and acceleration settings, respectively, to obtain platelet-rich plasma (PRP). Platelet-poor plasma (PPP) was prepared by further centrifugation of the remaining blood at 1500 xg for 10 minutes. Platelet counts were performed on the Coulter Counter (Coulter Electronics Inc.) and PRP was adjusted with PPP to a constant count of $3.0 \times 10^{-8}$/ml.

Platelet aggregation studies were performed at 37° C. on a dual channel aggregometer (Dayton Dual Channel Aggregation Module), at a stirring speed of 900 rpm. Optical density for PRP and PPP was set at 10% and 90%, respectively. Adenosine diphosphate (ADP) (0.05 ml) was added to 0.45 ml of stirred suspension of PRP up to the final concentration as shown. The maximal or steepest slope of the aggregation tracing curve was measured.

The maximal slope of the platelet aggregation tracing curve was computed using the equation: $Dfi = f(ti) - f(ti-1)/ti - t(i-1) = h\ max(cm)/t(min)$, where h max is the height of the steepest slope of the curve in centimeters, and t is the time of the steepest slope of the curve in minutes. Coefficient (r) values were computed using linear regression. In some computations, logarithm-transformed data were used.

The fluorescence measurements were obtained using the IDEXX Fluorescence Concentration Analyzer (FCA) machine (IDEXX Laboratories, Inc., Westbrook, Me.). This instrument uses a specially designed (96-2311) 2 mm diameter filter membrane-bottomed plate (Fluoricon assay plate) that separates antibody-bound cells from non-bound antibody in solution by applying a vacuum (0–25 mmHg) from below the membrane. The total cell/antibody-bound fluorescence is determined by front-surface fluorimetry. The instrument has a fluorimeter capable of exciting and reading at several wavelengths (400/450 nm-590/620 nm).

EXAMPLE 1

Fluorescence-conjugated Immunobinding Assay for Platelet Activation

Ten µl of phosphate buffer saline (PBS, 0.01 M, pH 7.4, as baseline) or ADP in a series of concentrations (10 µM, 25 µM, 50 µM, 100 µM and 150 µM) were added to a 90 µl sample of PRP in round-bottomed polystyrene tubes and allowed to incubate at room temperature for five minutes. Eighty µl of mixed sample was immediately added to a 1 ml final concentration of 1% of paraformaldehyde PBS solution in 1.5 ml vials, and the samples were incubated at 4° C. for four hours. The fixed samples were washed twice by centrifugation in a microcentrifuge using PBS solution. The washed platelets were diluted to $8.5 \times 10^{-7}$/ml in PBS solution.

A 20 µl aliquot of diluted samples was placed in 96 well plates. A 20 µl aliquot of 1:20 diluted CD62, or 1:40 diluted CD41a, or 1:50 diluted antifibrinogen Ab was added and the samples were incubated in the dark at room temperature for 30 minutes. The cells in the Fluoricon assay plates were concentrated and washed three times in washing buffer (1% Tween PBS) by applying a vacuum membrane from below the plates of 25 mm Hg in the Pandex FCA machine. This step removed any unbound antibody and free fluorescence marker from the complexes. Antibody-bound fluorescence was determined by reading plates at a gain of 1 for CD41a and antifibrinogen Ab and of 10 for CD62 on the FCA instrument at the appropriate wavelength. Data was recorded as relative fluorescence units (FU), after subtracting the blank.

In experiments designed to determine the optimal dilution of PRP and of fluorescence-conjugated antibodies, the same total volume, with varying dilutions of PRP and the antibodies, was used. For the determination of the time course change of platelet reactivity to ADP as measured by aggregation and by expression of P-selectin, PRP was stored at room temperature in the centrifuge tubes after being diluted to a constant concentration with PPP. At each time point, PRP was withdrawn from the stock tubes and added to test tubes and the activation and aggregation assays performed as described above. For the comparison of the present assay to the flow cytometric analysis, samples were prepared as described in flow cytometric analysis example, and 100 µl of the samples were placed in Fluoricon plates and read on the FCA instrument.

Figure 2:
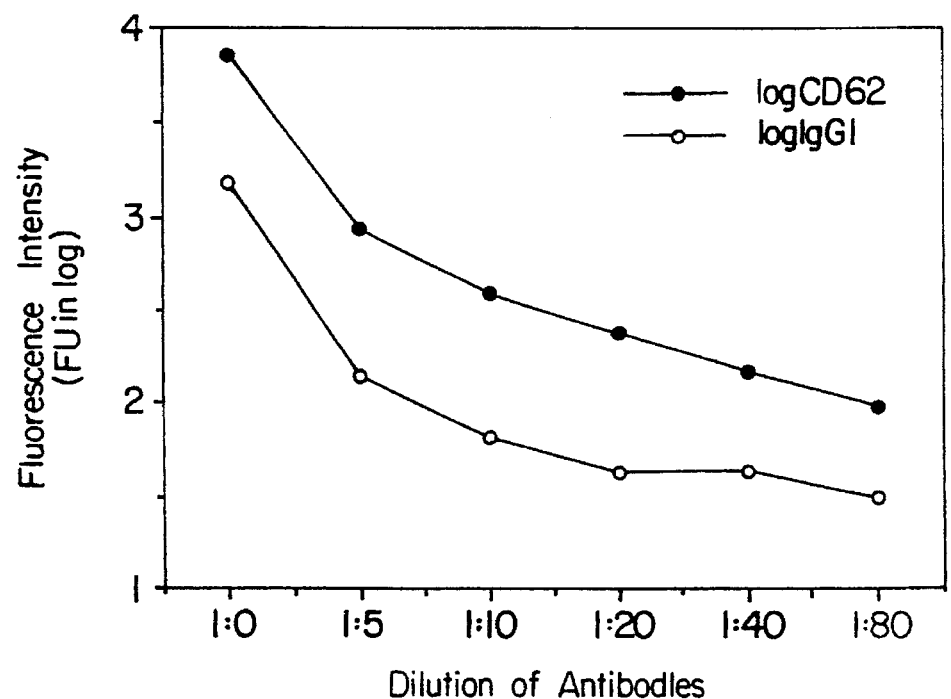
FIG. 2 is a graph depicting the fluorescence intensity of P-selectin in resting platelets detected in the present assay using various diluted anti-P-selectin antibody (CD62) and IgG1 (n=2) preparations. Platelets from two normal donors were sampled and tested in the assay using various dilutions of CD62 as indicated. Circles represent nonspecific binding (1gG1), whereas circles in bold represent specific binding (CD62). Fluorescence intensity was log-transformed.
Figure 3:
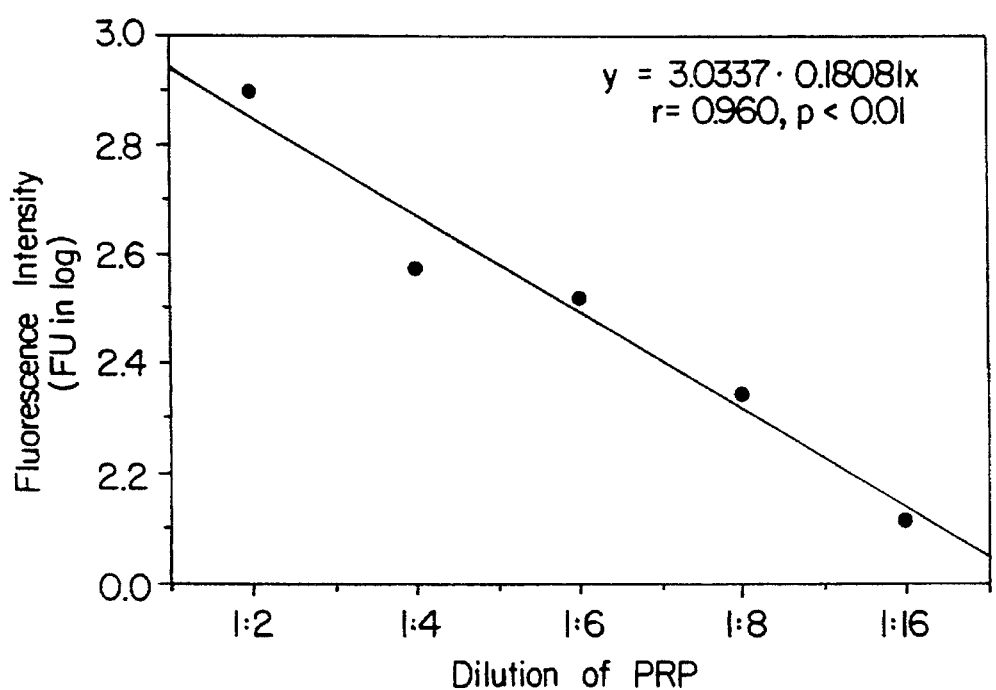
FIG. 3 is a graph depicting the fluorescence intensity in diluted resting platelets detected in the present assay using anti-P-selectin antibody (n=2), wherein samples from two normal donors were tested using CD62 diluted at 1:20 in volume. Fluorescence intensity was log-transformed and the coefficient r was computed using linear regression.
Figure 4:
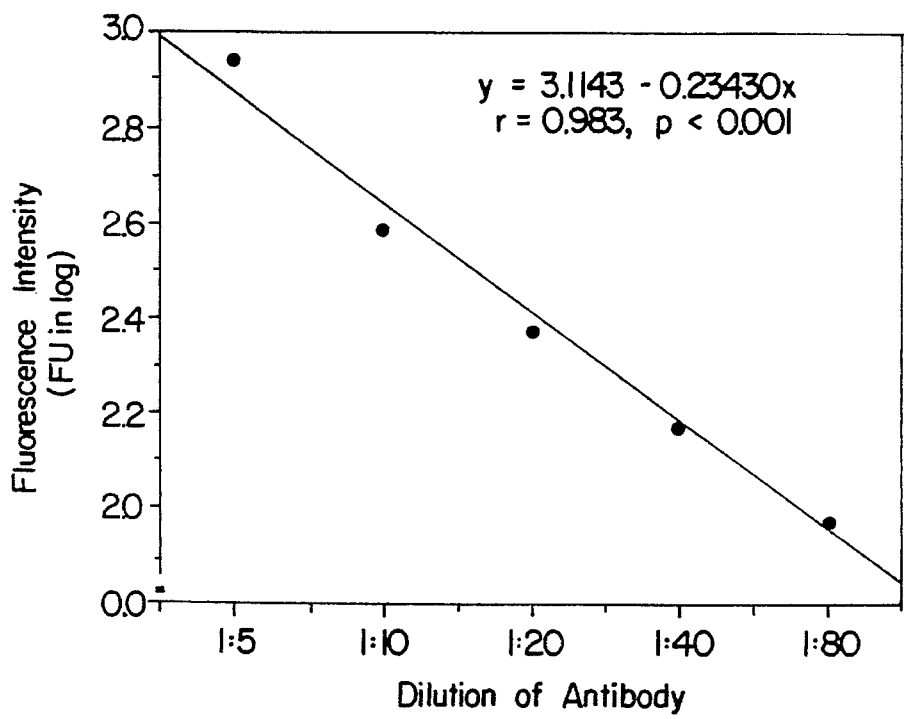
FIG. 4 is a graph depicting fluorescence intensity in resting platelets detected in the present assay using various dilutions of CD62 (n=2). Platelets from two normal donors were sampled and tested by the present assay. Log-transformed fluorescence intensity was used in the computation of the coefficient r using linear regression.
Figure 5:
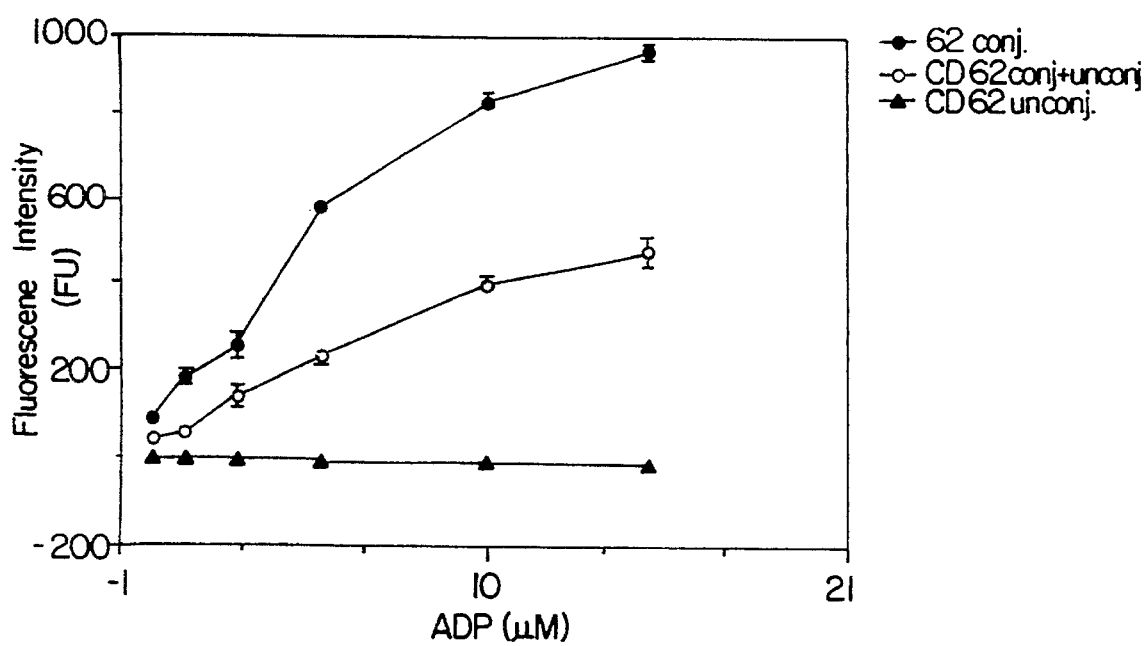
FIG. 5 is a graph depicting the fluorescence intensity in ADP-stimulated platelets in plasma detected using the present assay (n=2). Platelets were sampled from two normal donors and tested by the assay. Both phycoerythrin (PE)-conjugated and unconjugated CD62 were diluted to the same concentration. Closed circles represent the fluorescence intensities detected using PE-conjugated CD62, while triangles represent the values detected using unconjugated CD62, and the open circles represent the levels of fluorescence intensity detected by using unconjugated CD62 and PE-conjugated CD62.

To select the optimal conditions for the assay, various dilutions of antibody and antigen (platelets) were tested in the present assay. The selection of optimal conditions was based on selecting the concentration of the antibody that was on the steepest slope of the dilution curve and from which the most specific and the least non-specific reactions were obtained. Optimal conditions were obtained using anti-P-selectin antibody at a 20-fold dilution in volume or at an antibody/platelets ratio of 0.04 µg/1.5×10 e-6 cells. At this dilution, the specific reaction was greatest while demonstrating the lowest non-specific reaction (FIG. 2) and a wide range of concentrations of P-selectin was detectable in a dose-dependent manner (FIG. 3). Furthermore, it was in the middle of a linear dilution curve (FIG. 4), which makes the assay specific and sensitive. When the same amount of unconjugated monoclonal antibody to P-selectin was added to platelets in plasma followed by the addition of fluorescence-conjugated P-selectin antibody, fluorescence intensity of the platelets was decreased by 50%, indicating a satisfactory competitive inhibition of binding (FIG. 5).

Expression of P-selectin in four fixed platelet aliquots (mean levels: 56.00 to 60.00 FU/1.5×10 e-6 cells) from the same healthy subject were determined in ten replicates (for intra-assay variability) and in triplicates (for inter-assay variability) in multiple separate assays. The intra-assay CVs for the means of ten replicates ranged from 3.45% to 10.78% (mean: 6.97%). The time-based inter-assay CVs for the means of triplicates ranged from 5.93% to 2.39% (mean: 8.11%). The sample-based inter-assay CVs for the means of triplicates ranged from 2.82% to 13.99% (mean: 6.17%).

After incubation with CD62 for 30 minutes, a drop of platelets in plasma was transferred to a slide. Platelets were then evaluated by microscopy. ADP-activated platelets became larger, developed protrusions, and changed to a spherical shape under light microscopy. These activated platelets demonstrated red fluorescence under fluorescence microscopy.

EXAMPLE 2

Flow Cytometric Analysis

Platelet concentrates were obtained from the Mayo Clinic blood bank within 24 hours of collection of blood from volunteer donors. Platelet concentrate (PC) was prepared by collecting blood (450±45 ml) from random donors in 63 ml of CPD in a pyrogen-free (Fenwal Laboratories, Morton Grove, Ill.) quad blood collection pack with an attached satellite bag containing 100 ml of ADSOL solution. After blood collection, whole blood was centrifuged for 5.2 minutes at 1400 g's at 20°–24° C. The platelet-rich plasma was pressed into an empty satellite bag and spun for 20 minutes at 2500 g's at 20°–24° C. The platelet-poor plasma was pressed into an empty satellite bag, leaving approximately 50 ml of PC. The PC was left undisturbed for 1 hour, was resuspended on a platelet rotator, and stored on a horizontal flatbed shaker. Twenty individual PC units were sampled after 24 hours of storage.

Samples were prepared for analysis by fixing 100 µl of platelets with 1 ml cold 1% paraformaldehyde for 1 hour at 4° C. The platelets were washed (×2) with phosphate-buffered saline/EDTA (PBS/EDTA), the pellet was resuspended in 1 ml PBS/EDTA and stored at 4° C. in the dark. The following day (within 24 hours) 50 µl of the resuspended platelets were labeled with 10 µl of monoclonal antibody CD41 (AMAC, Inc., Westbrook, Me.). After a 10-minute incubation in the dark at room temperature (RT), 20 µl of MoA6 CD62 (Becton-Dickinson, San Jose, Calif.) was added and incubated 20 more minutes in the dark at 25° C. The sample was then washed (×1) with PBS/EDTA and the pellet was resuspended in 1 ml of cold 1% paraformaldehyde and stored at 4° C. in the dark for flow cytometric analysis. All samples were analyzed within 6 hours of labeling. Samples were analyzed on a flow cytometer (FACScan, Becton-Dickinson, Mountain View, Calif.) within 6 hours of labeling. The percentage of platelets expressing P-selectin (the percentage of activated platelets) was determined as described by R. Funbeer et al. *Transfusion*, 30, 20 (1990). The mean GPIIb-IIIa surface density was determined for the subsets of P-selectin-negative platelets and P-selectin-positive platelets. See, H. M. Rinder et al., *Transfusion*, 31, 409 (1991); *Anesthesiology*, 75, 963 (1991).

Figure 6:
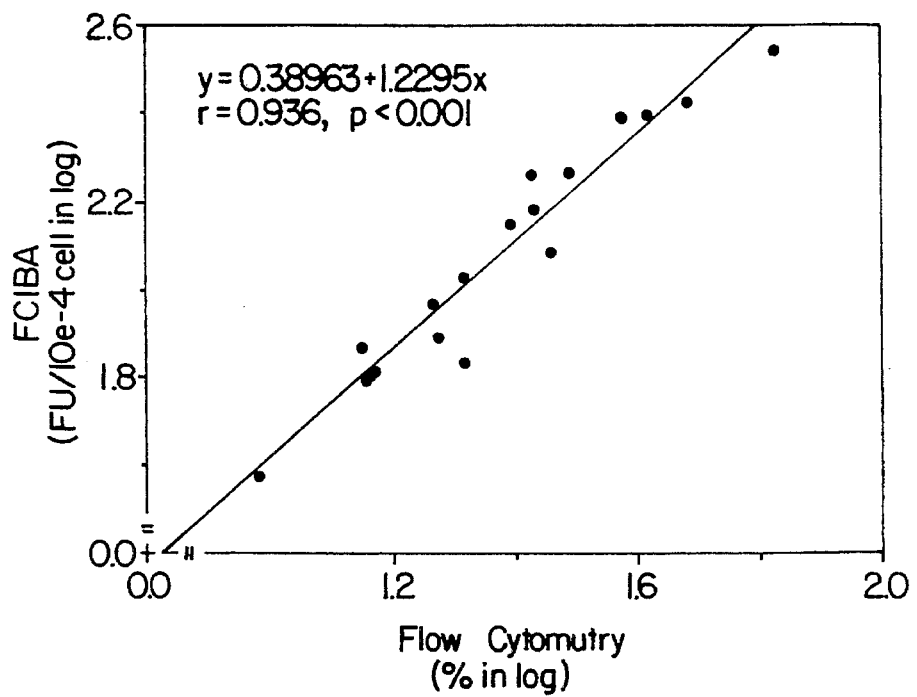
FIG. 6 is a graphic correlation of the present assay with flow cytometric analysis in determination of P-selectin in platelets in platelet concentrates (n=20). Platelets were sampled from 20 normal donors' platelet concentrates using the present assay and flow cytometric analysis simultaneously. A value of r=0.936 was obtained from the linear regression, indicating the positive association between the two assays (p<0.001).

Quantitative expression of P-selectin as fluorescence intensity or as the ratio of P-selectin positively stained platelets in one-day stored platelets in platelet concentrates from 20 normal donors were determined simultaneously by the present assay and by flow cytometric analysis, respectively. Linear regression analysis of the data showed that the log-transformed fluorescence intensity of P-selectin as determined in FCIBA was correlated with the ratio of P-selectin positively stained platelets expressed as a log-transformed ratio as measured in flow cytometric analysis (r=0.936, p<0.001) (FIG. 6).

EXAMPLE 3

Induction of Expression of P-selectin and Aggregation in Platelets by ADP

Figure 7:
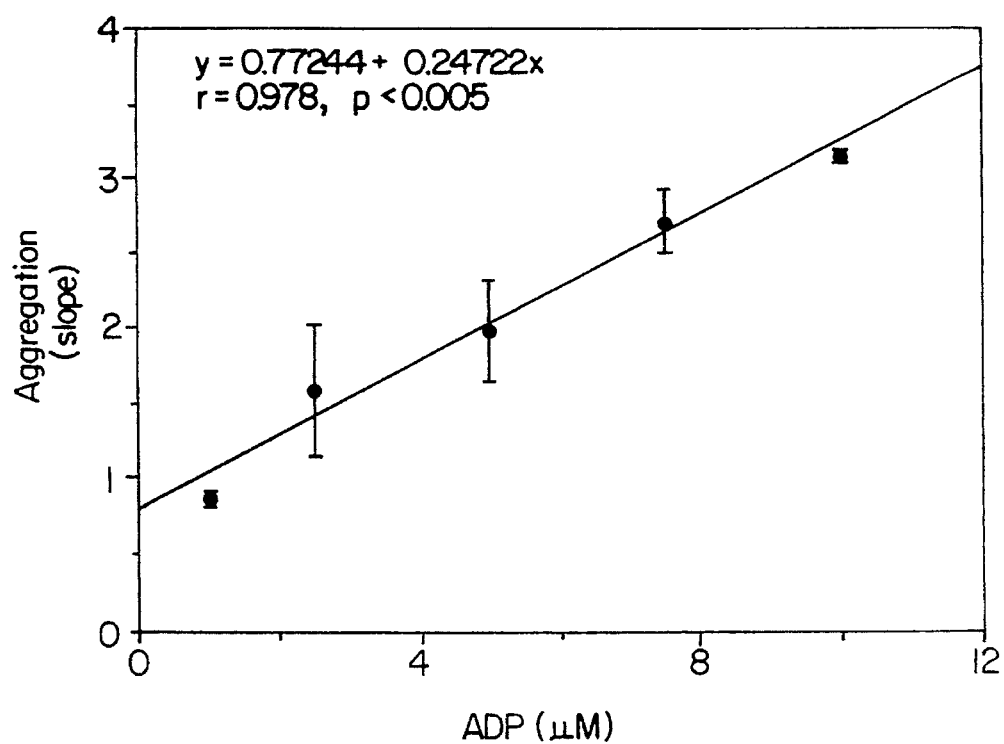
FIG. 7 is a graph depicting the platelet aggregation slopes with stimulating doses of ADP as measured in an aggregometer (n=3). Platelet aggregation in plasma was performed in triplicate by aggregometry. The slopes were the means of the steepest slopes of aggregation tracing curves in response to each dose of ADP.
Figure 8:
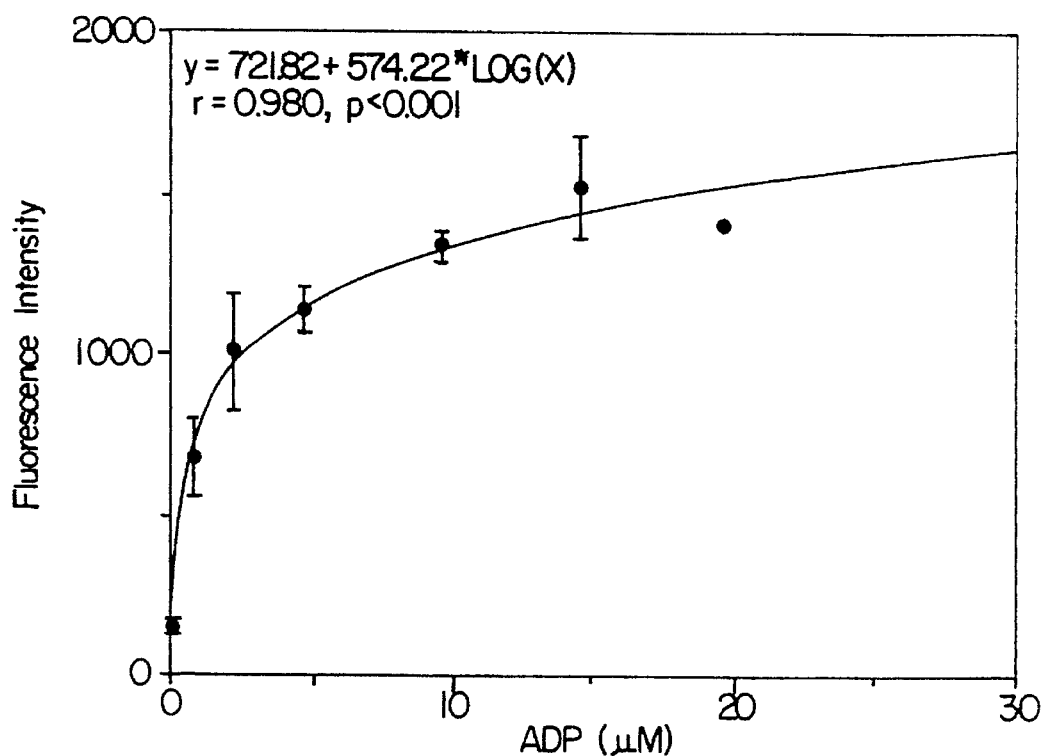
FIG. 8 is a graph demonstrating association between the expression of P-selectin and stimulating concentrations of ADP assayed in the present assay (n=3). Final concentrations of ADP in platelets in plasma were used.

Platelets in plasma from three healthy subjects aggregated in the aggregometer in response to ADP in a dose-dependent manner (FIG. 7), and the steepest slopes of the aggregation tracing curves were correlated with increasing stimulating doses of ADP (FIG. 7). P-selectin in platelets in plasma from the same three healthy subjects was also translocated to the plasma membrane of platelets in response to ADP in a dose-dependent manner, as measured by phycoerythrin-fluorescence with increasing stimulating doses of ADP, in accord with Example 2 (FIG. 8).

EXAMPLE 4

Time Course Change of Platelet Reactivity to ADP

Figure 9:
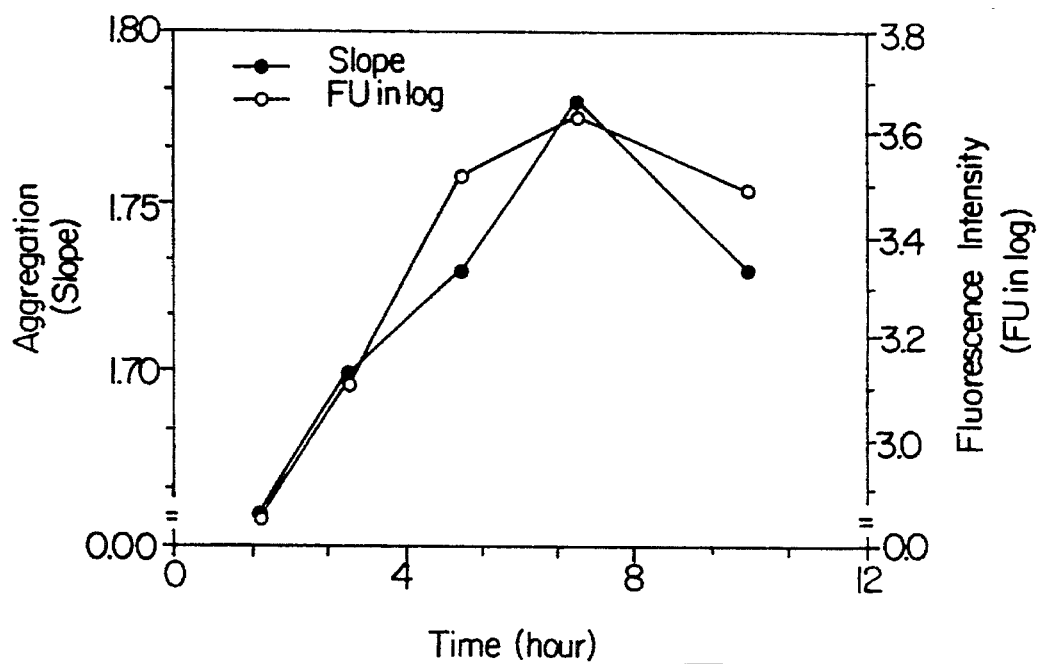
FIG. 9 is a depiction of the time course change of platelet reactivity to ADP as measured by aggregation in aggregometer and by expression of P-selectin as detected by the present assay (n=3). Platelets from three normal donors were sampled and assayed by aggregometry and by the present assay simultaneously. The hour indicated is the storage time of platelets after blood was drawn. The steepest slopes of aggregation-tracing curves and log-transformed fluorescence intensity were used.

Reactivity of platelets in plasma to ADP as measured by aggregation or by expression of P-selectin from three healthy donors were measured both by an aggregometer and by the procedure of Example 1, at time intervals ranging from 1.5 to 10 hours after blood was drawn. Platelets in plasma aggregated in response to increasing stimulating doses of ADP in parallel with the expression of P-selectin at time intervals (FIG. 9). The reactivity of platelets to ADP was increased at time intervals, and reached similar peak levels at the seventh hour (FIG. 9).

EXAMPLE 5

Relation of ADP-induced Aggregation and Expression of P-selectin in Platelets

Figure 10:
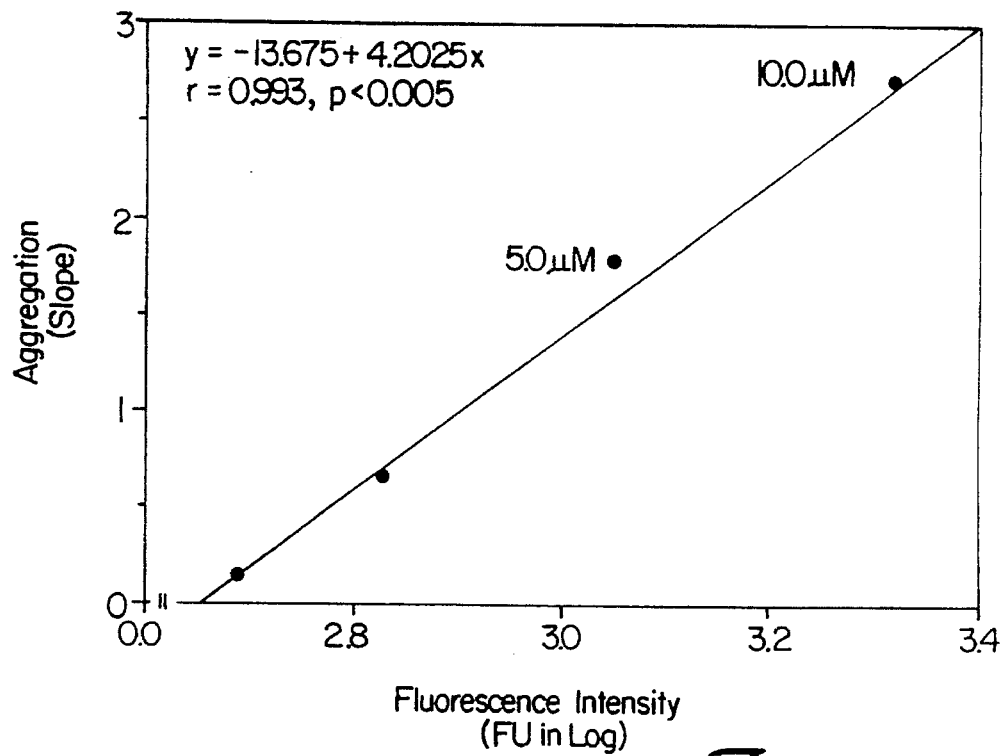
FIG. 10 depicts the correlation of platelet aggregation by aggregometry with the expression of P-selectin as determined by the present assay in ADP-stimulated platelets in plasma (n=3). Platelets from three normal donors were assayed in triplicate by aggregometry and by the present assay simultaneously. The doses of ADP used are as indicated. Coefficient r was computed using linear regression.
Figure 11:
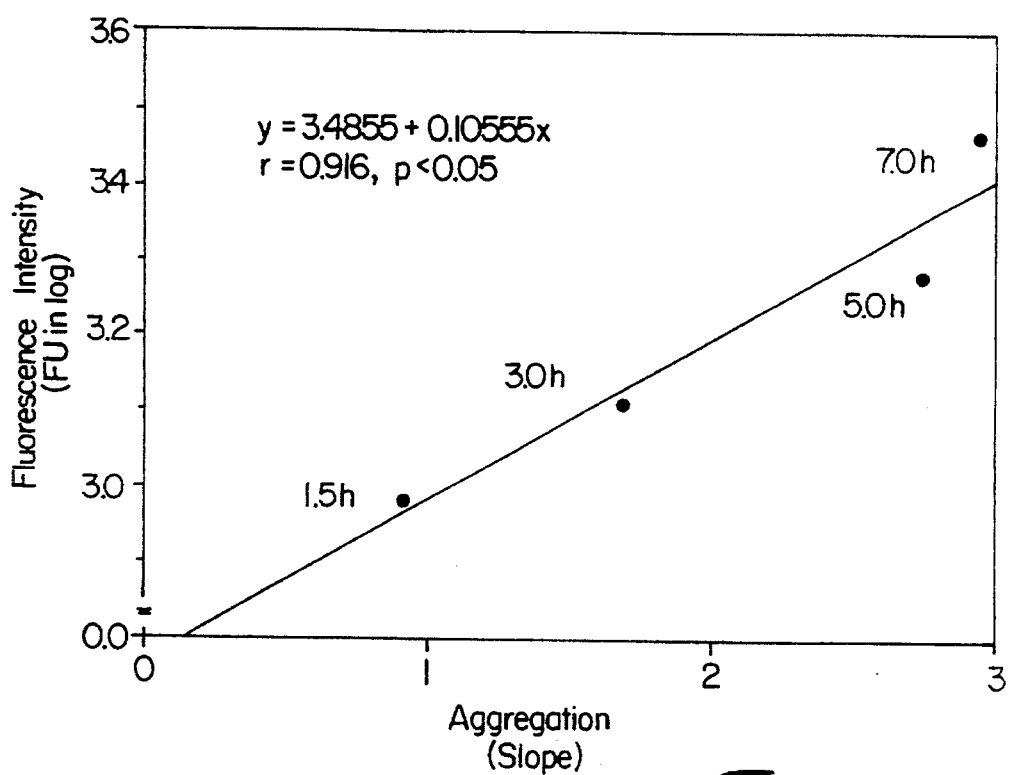
FIG. 11 depicts the correlation of expression of P-selectin by the present assay with aggregation by aggregometry in ADP-stimulated platelets in plasma at time intervals (n=3). A dose of 2.5 µM of ADP was used in the determination of aggregation by aggregometry and by the present assay in platelets in plasma sampled from three normal donors. Values are the means±standard deviation (SD) of three samples in triplicate. Coefficient r was computed using linear regression.

Data from Examples 3–4 were analyzed using linear regression. This showed that the expression of P-selectin in platelets in plasma as measured by the present assay was correlated positively with platelet aggregation of platelets in plasma as determined by aggregometry in response to ADP both on the basis of stimulating doses of ADP (FIG. 10) and on the basis of time intervals (FIG. 11).

EXAMPLE 6

Figure 12:
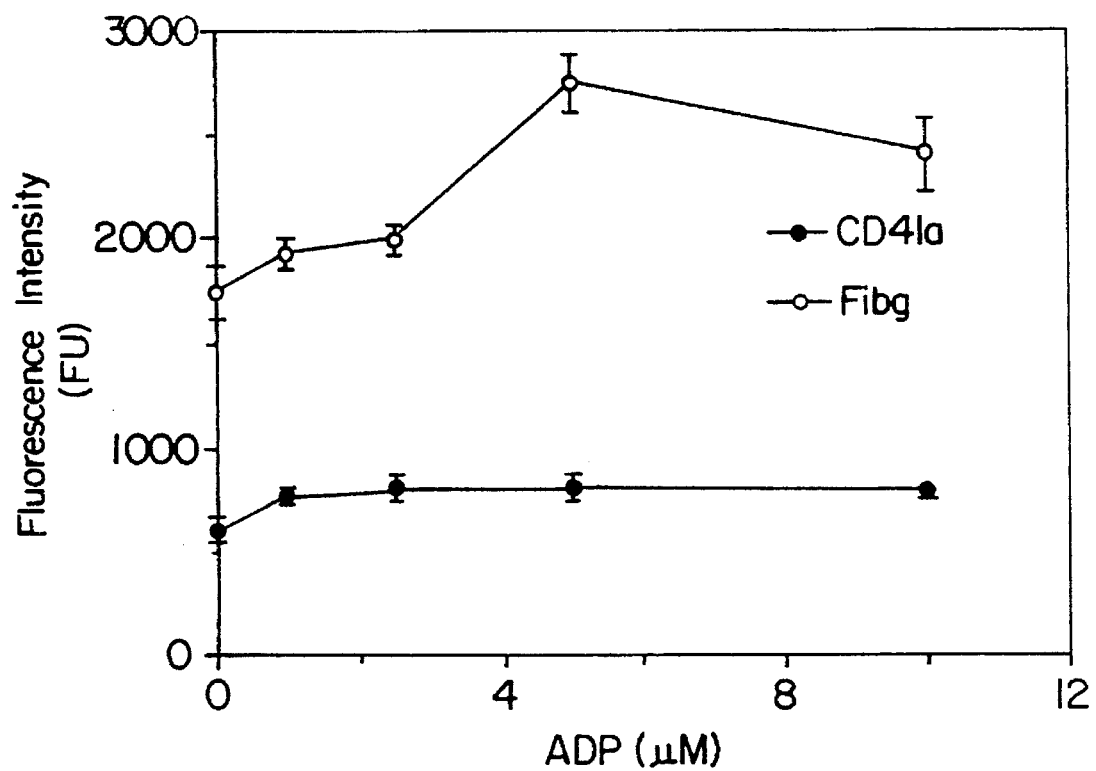
FIG. 12 depicts expression of GPIIb-IIIa complex and fibrinogen on the surface of ADP-stimulated platelets in plasma (n=3). ADP-stimulated platelets in plasma from three normal donors were sampled and assayed by the present assay. Values are the means±SD of three samples in triplicate.

Relation of Expression of P-selectin and Exposure of GPIIb-IIIa and Fibrinogen in Platelets in Response to ADP To determine the alterations in the amount of GPIIb-IIIa complex and P-selectin expressed on the platelet surface and in levels of fibrinogen bound to platelets or exposed on platelets in response to the stimulation of ADP, platelets in plasma from two healthy subjects were sampled and tested in the assay of Example 1 simultaneously by using monoclonal antibodies to GPIIb-IIIa as well as with monoclonal antibodies to P-selectin, and a polyclonal antibody to fibrinogen. Detectable GPIIb-IIIa complex in platelets showed little change in response to stimulation with ADP (FIG. 12). In contrast, the levels of fibrinogen bound to platelets or exposed on the surface of platelets in response to increasing doses of ADP was increased and reached a peak level at a dose of 5.0 µM of ADP (FIG. 12). In platelets in plasma, the changes in the amount of detectable GIIb-IIIa complex correlated weakly with alteration in the levels of bound or exposed fibrinogen in response to the stimulating doses of ADP ranging from 0.0 to 10.0 µM ($y=355.64+3.29 X$, $r=0.45$, $p>0.05$), and also correlated only weakly with the alteration in levels of expressed P-selectin ($y=269.47+170.44 * \log (X)$, $r=0.663$, $p>0.05$). The alteration in levels of fibrinogen bound to platelets or exposed on the surface of platelets was correlated more strongly with changes in levels of P-selectin expressed in response to the increasing stimulating doses of ADP ranging from 0.0 to 10.0 µM ($y=167.3+0.44 X$, $r=0.858$, $P<0.05$), suggesting the association of P-selectin with the binding or exposure of fibrinogen on ADP-stimulated platelets.

Detection of P-selectin translocation to the platelet surface as determined by the present method is a sensitive and specific measure of platelet activation, which correlates well with more complex traditional measures of this phenomenon. Although simpler cells could be employed for fluorometry, the methodology using microtiter plates with filters and the measurement of front-surface fluorimetry to measure this translocation permits measurements to be made in 96 wells as a single semiautomated procedure. For further expansion of the analytic capacity, a fluorescence analyzer with the ability to read 10 plates (960 wells) as an even more automated procedure (screen machines, IDEXX, Portland, Me.) is also available. These features make the present method very practical for the study of the dynamics of platelet activation in the clinical disease states discussed above.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A fluorometric method for measuring platelet activation in a sample of platelets which is not exogenously activated comprising:

(a) isolating in vitro a first sample of physiological material comprising platelets and a second sample of physiological material comprising platelets from a mammal, wherein said sample each contains a preselected number of platelets;

(b) adding an amount of an activation agonist to said first sample in a liquid medium for a period of time effective to maximally activate the activatable platelets in said first sample; while maintaining the second sample in a liquid medium for an equivalent period of time;

(c) forming binary labelled complexes with the activated platelets in each sample by adding to each sample an amount of
      (i) an anti-P-selectin antibody conjugated to a fluorescent label; or
      (ii) an anti-P-selectin antibody conjugated to a binding site for a detectable label followed by a detectable fluorescent label which specifically binds to said binding site; and (d) determining the fluorescence of the binary labelled complexes in each sample, wherein a ratio of the fluorescence of said second sample to said first sample provides a measure of the extent of platelet activation in said second sample.

2. The method of claim 1 wherein the samples isolated in step (a) are adjusted to contain essentially the same number of platelets.

3. The method of claims 1 or 2 wherein the mammal is a human.

4. The method of claim 3 wherein the platelets are isolated from a sample of blood.

5. The method of claim 4 wherein said first and second samples comprise platelet-rich plasma.

6. The method of claim 4 wherein the activation agonist is adenosine 5'-diphosphate.

7. The method of claim 1 wherein the platelets in said samples are fixed following step (b).

8. The method of claim 1 wherein said liquid medium comprises phosphate-buffered saline.

9. The method of claim 1 wherein the anti-P-selectin antibody is monoclonal antibody CD62.

10. The method of claim 9 wherein said monoclonal antibody CD62 is fluoresceinated.

* * * * *